United States Patent
Bishop et al.

(10) Patent No.: US 12,423,473 B2
(45) Date of Patent: Sep. 23, 2025

(54) ANONYMISING ROBOTIC DATA

(71) Applicant: CMR SURGICAL LIMITED, Cambridge (GB)

(72) Inventors: Steven Bishop, Cambridge (GB); Ricardo Michael Henderson da Silva, Cambridge (GB)

(73) Assignee: CMR SURGICAL LIMITED, Cambridge (GB)

( * ) Notice: Subject to any disclaimer, the term of this patent is extended or adjusted under 35 U.S.C. 154(b) by 225 days.

(21) Appl. No.: 16/925,357

(22) Filed: Jul. 10, 2020

(65) Prior Publication Data
US 2021/0012032 A1 Jan. 14, 2021

(30) Foreign Application Priority Data
Jul. 11, 2019 (GB) ..................................... 1909992

(51) Int. Cl.
*G06F 21/62* (2013.01)
*A61B 34/35* (2016.01)
(Continued)

(52) U.S. Cl.
CPC .......... *G06F 21/6254* (2013.01); *A61B 34/35* (2016.02); *A61B 34/37* (2016.02); (Continued)

(58) Field of Classification Search
CPC ............. G06F 21/6245; G06F 21/6254; H04L 9/0894; H04L 2209/42; H04L 2209/88;
(Continued)

(56) References Cited

U.S. PATENT DOCUMENTS 8,462,681 B2 * 6/2013 Pochiraju .............. H04L 67/125
370/465
11,069,036 B1 * 7/2021 Simhadri ................ G06T 7/248
(Continued)

FOREIGN PATENT DOCUMENTS

CN 101987039 A 3/2011
CN 106999257 A 8/2017
(Continued)

OTHER PUBLICATIONS

Munzer, B. et al., 'Domain-Specific Video Compression for Long-Term Archiving of Endoscopic Surgery Videos', 2016 IEEE 29th International Symposium on Computer-Based Medical Systems, 2016, 312-317 (Year: 2016).*
(Continued)

*Primary Examiner* — Luu T Pham
*Assistant Examiner* — Paul J Skwierawski
(74) *Attorney, Agent, or Firm* — Lando & Anastasi, LLP

(57) ABSTRACT

A method is provided of anonymising data in a surgical robotic system. The surgical robotic system comprises a robot having a base and an arm extending from the base to an attachment for an instrument, the arm comprising a plurality of joints whereby the configuration of the arm can be altered. The method comprises receiving a data stream captured by the surgical robotic system, the data stream comprising data relating to a surgical procedure and comprising personally-identifiable data; determining one or more personally-identifiable feature in the received data stream; and generating, in dependence on the determined personally-identifiable feature and the received data stream, an anonymised data stream omitting the personally-identifiable data.

19 Claims, 8 Drawing Sheets

(51) Int. Cl.
| | |
|---|---|
| *A61B 34/37* | (2016.01) |
| *G06N 20/00* | (2019.01) |
| *G16H 20/40* | (2018.01) |
| *G16H 30/40* | (2018.01) |
| *G16H 40/67* | (2018.01) |
| *H04L 9/40* | (2022.01) |
| *H04N 19/136* | (2014.01) |
| *A61B 34/30* | (2016.01) |

(52) U.S. Cl.
CPC .............. *G06N 20/00* (2019.01); *G16H 20/40* (2018.01); *G16H 30/40* (2018.01); *G16H 40/67* (2018.01); *H04L 63/0421* (2013.01); *H04N 19/136* (2014.11); *A61B 2034/301* (2016.02)

(58) Field of Classification Search
CPC .............. H04L 2463/121; H04L 65/762; H04L 65/765; H04L 67/125; A61B 34/30; A61B 34/35; G16H 15/00; G16H 10/60; G16H 20/40; G16H 30/20; G16H 30/40; G16H 40/60; H04N 19/169
See application file for complete search history.

(56) References Cited

U.S. PATENT DOCUMENTS

| | | | |
|---|---|---|---|
| 11,132,462 B2* | 9/2021 | Shelton, IV | G06F 21/6254 |
| 2010/0278086 A1 | 11/2010 | Pochiraju et al. | |
| 2012/0177256 A1 | 7/2012 | Keefe et al. | |
| 2012/0307027 A1* | 12/2012 | Popovic | A61B 34/30 901/46 |
| 2014/0051921 A1 | 2/2014 | Miller et al. | |
| 2014/0188514 A1* | 7/2014 | Balignasay | G16H 10/60 705/3 |
| 2014/0287393 A1* | 9/2014 | Kumar | G09B 5/02 434/262 |
| 2015/0134365 A1 | 5/2015 | Keefe et al. | |
| 2015/0256790 A1* | 9/2015 | Priest | H04N 5/268 348/441 |
| 2017/0249432 A1* | 8/2017 | Grantcharov | G06F 1/12 |
| 2017/0255751 A1 | 9/2017 | Sanmugalingham | |
| 2018/0122506 A1 | 5/2018 | Grantcharov et al. | |
| 2018/0271615 A1 | 9/2018 | Mahadik et al. | |
| 2019/0183591 A1 | 6/2019 | Johnson et al. | |
| 2019/0201136 A1* | 7/2019 | Shelton, IV | A61B 17/320068 |
| 2019/0205441 A1 | 7/2019 | Shelton, IV et al. | |
| 2019/0205566 A1 | 7/2019 | Shelton, IV et al. | |
| 2019/0206562 A1 | 7/2019 | Shelton, IV et al. | |
| 2020/0107891 A1* | 4/2020 | Ohashi | G06T 1/0014 |
| 2020/0222133 A1 | 7/2020 | Shuma et al. | |
| 2020/0372180 A1* | 11/2020 | Venkataraman | G06F 21/6254 |
| 2021/0012032 A1 | 1/2021 | Bishop et al. | |

FOREIGN PATENT DOCUMENTS

| | | | | |
|---|---|---|---|---|
| CN | 107615395 A | | 1/2018 | |
| CN | 108453742 A | | 8/2018 | |
| CN | 109063506 A | * | 12/2018 | ......... G06F 21/6245 |
| EP | 3505042 A1 | * | 7/2019 | ......... A61B 1/00011 |
| EP | 3506299 A1 | * | 7/2019 | ......... G06F 21/6254 |
| JP | 2005135344 A | | 5/2005 | |
| JP | 2014166298 A | | 9/2014 | |
| JP | 2015532040 A | | 11/2015 | |
| JP | 2018047088 A | | 3/2018 | |
| KR | 10-2019-0000107 A | | 1/2019 | |
| RU | 2412799 C2 | | 2/2011 | |
| RU | 2412800 C2 | | 2/2011 | |
| RU | 2601199 C2 | | 10/2016 | |
| RU | 2662883 C2 | | 7/2018 | |
| RU | 2672524 C2 | | 11/2018 | |
| WO | 2016044920 A1 | | 3/2016 | |
| WO | 2016149794 A1 | | 9/2016 | |
| WO | 2019133059 A1 | | 7/2019 | |
| WO | 2020044857 A1 | | 3/2020 | |
| WO | 2021005380 A1 | | 1/2021 | |
| WO | 2021005381 A1 | | 1/2021 | |
| WO | WO-2023278965 A1 | * | 1/2023 | |

OTHER PUBLICATIONS

Indian Examination Report from corresponding Indian Application No. 202227007050 dated Jun. 29, 2022.
Notification of Transmittal of the International Search Report and the Written Opinion of the International Searching Authority from corresponding PCT/GB2020/051678 dated Sep. 15, 2020.
United Kingdom Search Report from corresponding United Kingdom Application No. GB1909992.8 dated Dec. 11, 2019.
Cummins, J. et al. "Steganography and Digital Watermarking," School of Computer Science, The University of Birmingham, Copyright 2004, Version 1.2, pp. 1-23.
Notification of Transmittal of the International Search Report and the Written Opinion of the International Searching Authority from corresponding PCT/GB2020/051677 dated Oct. 2, 2020.
United Kingdom Examination Opinion from corresponding United Kingdom Application No. GB2002390.9 dated Jul. 31, 2020.
United Kingdom Examination Report from corresponding United Kingdom Application No. GB1909992.8 dated Sep. 1, 2022.
Australian Examination Report No. 1 from corresponding Australian Application No. 2020309810 dated Mar. 6, 2023.
Eadie, L. et al., "Telemedicine in surgery", British Journl of Surgery 2003, 90: 647-658.
Loukas, C., "Video content analysis of surgical procedures", Surgical Endoscopy, Oct. 26, 2017, 32: 553-568.
Japanese Notification of Reason for Rejection from corresponding Japanese Application No. 2022-500999 dated Feb. 21, 2023.
Japanese Notification of Reason for Rejection from corresponding Japanese Application No. 2022-500997 dated Feb. 3, 2023.
Australian Examination Report No. 1 from corresponding Australian Application No. 2020311031 dated Feb. 24, 2023.
Munzer B. et al., "Domain-Specific Video Compression for Long-term Archiving of Endoscopic Surgery Videos," 2016 IEEE 29th International Symposium on Computer-Based Medical Systems, pp. 312-317.
Australian Examination Report No. 2 from corresponding Australian Application No. 2020309810 dated Aug. 2, 2023.
Australian Examination Report No. 2 from corresponding Australian Application No. 2020311031 dated Aug. 21, 2023.
Japanese Notification of Reason for Rejection from corresponding Japanese Application No. 2022-500997 dated Aug. 22, 2023.
Monteiro et al., "A machine learning methodology for medical imaging anonymization" Aug. 25-29, 2015 2015 37th Annual International Conference of the IEEE Engineering in Medicine and Biology Society (EMBC) DOI: 10.1109/EMBC.2015.7318626 https://ieeexplore.ieee.org/abstract/document/7318626.
Russian Office Action from corresponding Russian Application No. 2022103245 dated Jan. 24, 2024.
Russian Search Report from corresponding Russian Application No. 2022103245 dated Jan. 23, 2024.
Russian Office Action from corresponding Russian Application No. 2022103251 dated Mar. 27, 2024.
Russian Search Report from corresponding Russian Application No. 2022103251 dated Mar. 26, 2024.
Indian Hearing Notice from corresponding Indian Application No. 202227007048 dated Oct. 9, 2024.
United Kingdom Examination Report from corresponding United Kingdom Application No. GB2002390.9 dated Nov. 2, 2023.
Chinese Office Action from corresponding Chinese Application No. 202080050640.7 dated Jan. 25, 2025.
European Examination Report from corresponding European Application No. 20742407.8 dated Mar. 19, 2025.
European Examination Report from corresponding European Application No. 20742408.6 dated Apr. 7, 2025.

* cited by examiner

ANONYMISING ROBOTIC DATA

CROSS-REFERENCE TO RELATED APPLICATION

This application claims the benefit under 35 U.S.C. § 119 of United Kingdom Patent Application No. 1909992.8 filed on Jul. 11, 2019 which is hereby incorporated herein by reference in its entirety for all purposes.

FIELD OF THE INVENTION

This invention relates to anonymising patient data captured by a surgical robotic system during a surgical procedure performed by the surgical robotic system.

BACKGROUND

It is known to use robots for assisting and performing surgery. FIG. 1 illustrates a typical surgical robot 100 which consists of a base 108 and an arm 102. An instrument 105 is coupled to the arm. The base supports the robot, and is itself attached rigidly to, for example, the operating theatre floor, the operating theatre ceiling or a trolley. The arm extends between the base and the instrument. The arm is articulated by means of multiple flexible joints 103 along its length, which are used to locate the surgical instrument in a desired location relative to the patient. The surgical instrument is attached to the distal end 104 of the robot arm. The surgical instrument penetrates the body of the patient 101 at a port 107 so as to access the surgical site. As illustrated, at its distal end, the instrument comprises an end effector 106 for engaging in a medical procedure. The term 'instrument' encompasses an endoscope for imaging a surgical site.

The surgical robot 100 is controlled remotely by an operator (e.g. surgeon) via an operator console 200 shown in FIG. 2. The operator console 200 may be located in the same room (e.g. operating theatre) as the surgical robot 100 or remotely from it. The operator console 200 comprises input devices 202, 204 for controlling the state of the arm 102 and/or the instrument 105 attached thereto. The input devices 202, 204 may be handgrips or hand controllers mounted on parallelogram linkages. A control system converts the movement of the hand controllers into control signals to move the arms, joints and/or instrument end effector of a surgical root. The operator console 200 also comprises a display 206. The display 206 is arranged to be visible to a user operating the input devices 202, 204. The display is used to display a video stream of the surgical site (e.g. endoscope video).

Some surgical procedures may require several surgical robots, each one carrying an instrument or other implement which is used concurrently with the others at the surgical site. FIG. 3 illustrates a surgical robotic system 300 with multiple robots 302, 304, 306 operating in a common workspace on a patient 308. For example, surgical robots are often used in endoscopic surgery (e.g. laparoscopic surgery), which also may be referred to as minimally invasive surgery. As is known to those of skill in the art, during an endoscopic procedure the surgeon inserts an endoscope through a small incision or natural opening in the body, such as, but not limited to, the mouth or nostrils. An endoscope is a rigid or flexible tube with a camera attached thereto that transmits real-time images to a video monitor (e.g. display 206) that the surgeon uses to help guide their tools through the same incision/opening or through a different incision/opening. The endoscope allows the surgeon to view the relevant area of the body in detail without having to cut open and expose the relevant area. This technique allows the surgeon to see inside the patient's body and operate through a much smaller incision than would otherwise be required for traditional open surgery. Accordingly, in a typical robotic endoscopic surgery there is an endoscope attached to one surgical robot arm and one or more other surgical instruments, such as a pair of pincers and/or a scalpel, attached to one or more other surgical robot arms.

FIG. 4 illustrates an example endoscope 400 which is attachable to the end of a robot arm for use in minimally invasive surgery. The endoscope 400 has a distal end 402 for insertion into the surgical site of the patient, and a proximal end 404. The distal end 402 is connected to the proximal end 404 by an elongate shaft 406. The proximal end 404 comprises an interface 408 for engaging the end of the robot arm. The endoscope 400 has a power source and a light source for illuminating the surgical site. The endoscope 400 also has a data line for extracting the image data from the surgical site. These may all be attached to the proximal end 404 of the endoscope 400 independently and externally of the robot arm, as shown in FIG. 4. In FIG. 4, power is applied through stem 412, image data is extracted through stem 412, and light is applied through light stem 410. In an alternative implementation, any one or more of the light input, power input and data output may be applied/extracted to the endoscope through the robot arm. The endoscope 400 mounts to the end of the robot arm. The endoscope interface 408 engages a complementary interface of the robot arm. The endoscope 400 is attachable to and detachable from the robot arm via the robot arm and endoscope interfaces. In some cases, the endoscope 400 is operable independently of the robot arm in its detached state. In other words, in these cases the endoscope 400 can be operated manually by a member of the operating room staff when detached from the robot arm.

In addition to the images captured by the endoscope (which may be collectively referred to herein as the endoscope video) being used during surgery, the images captured by the endoscope may be recorded and subsequently used for a variety of purposes such as, but not limited to, learning and/or teaching surgical procedures, and assessing and/or reviewing the performance of the surgeon (by a third party or by the surgeon themselves).

In addition to the endoscope video, telemetry from the robotic system, data relating to the state of the robotic system and audio in the operating room and/or adjacent a control console can be captured. Such captured data can be used separately or in combination to assist with reviewing a procedure for learning and/or teaching purposes. Such captured data can include data identifying those involved in the procedures, including patients. It would be useful to be able to anonymise such captured data so that the anonymised data can be used more widely for teaching, performance assessment/review etc., without adversely affecting the privacy of those identified in the captured data.

SUMMARY

This summary is provided to introduce a selection of concepts that are further described below in the detailed description. This summary is not intended to identify key features or essential features of the claimed subject matter, nor is it intended to be used to limit the scope of the claimed subject matter.

According to an aspect of the present invention there is provided a method of anonymising data in a surgical robotic system, the surgical robotic system comprising a robot having a base and an arm extending from the base to an attachment for an instrument, the arm comprising a plurality of joints whereby the configuration of the arm can be altered, the method comprising:

receiving a data stream captured by the surgical robotic system, the data stream comprising data relating to a surgical procedure and comprising personally-identifiable data;

determining one or more personally-identifiable feature in the received data stream; and generating, in dependence on the determined personally-identifiable feature and the received data stream, an anonymised data stream omitting the personally-identifiable data.

The data stream may comprise one or more data channel from a group of data channels comprising:

video data received from an endoscope coupled to the surgical robotic system;

audio data recorded in respect of a surgical procedure;

telematics data corresponding to the surgical robotic system; and state data comprising the state of at least a portion of the surgical robotic system.

The personally-identifiable feature may be determined in dependence on the one or more data channel. The personally-identifiable feature may be determined in dependence on a first data channel of the group of data channels, and generating the anonymised data stream comprises modifying a second data channel of the group of data channels. The personally-identifiable feature may be determined in dependence on a first data channel of the group of data channels, and generating the anonymised data stream comprises modifying the first data channel.

Generating the anonymised data stream may comprise, in dependence on the determined personally-identifiable feature, one or more of: removing a data portion from the received data stream, the removed data portion comprising personally-identifiable data, and masking a data portion of the received data stream, the masked data portion comprising personally-identifiable data. Masking the data portion may comprise one or more of: blurring the data portion; and replacing values of data in the data portion with mask values. The data portion may comprise one or more partial frame of data. The data portion may comprise one or more frame of data. Determining the personally-identifiable feature may comprise determining a partial frame of data to which the personally-identifiable feature relates.

Generating the anonymised data stream may comprise saving a subset of the received data stream. The personally-identifiable feature may be determined in dependence on one or more of: an attachment state of an instrument, an operational state of an instrument attached to the arm, an operational state of the robot, a configuration of the arm and/or of an instrument attached to the arm, and a control state of the control console.

The personally-identifiable feature may be determined in dependence on one or more of: an instrument sensor signal received from an instrument sensor, the instrument sensor being configured to detect an instrument passing through a port providing access to a surgical site; whether the video data comprises a circle that grows or shrinks; whether the video data comprises a port-identifying feature; whether the video data comprises an image of a face; a measure of image white balance; a measure of image spectrum; a measure of image gradient from centre to edge; a procedure being performed; and a machine learning algorithm that has been trained using a plurality of known personally-identifiable features.

The anonymised data stream may be generated as the surgical procedure is being performed. Generating the anonymised data stream may comprise modifying the data portion for a time period that is one of: before the personally-identifiable feature is determined, after the personally-identifiable feature is determined, both before and after the personally-identifiable feature is determined, and between two personally-identifiable features.

The received data stream may comprise two or more data channels from the group of data channels, and the method may comprise generating the anonymised data stream by modifying the data portion in respect of at least two of the data channels separately.

The method may comprise: generating the anonymised data stream in real time or substantially real time; sending the anonymised data stream to a remote processor thereby enabling the remote processor to perform real time or substantially real time analysis of the anonymised data stream; and receiving from the remote processor in real time or substantially real time the result of the analysis for assisting an operator of the surgical robotic system.

According to another aspect of the present invention there is provided a data anonymiser system for a surgical robotic system for anonymising data from the surgical robotic system, the surgical robotic system comprising a robot having a base and an arm extending from the base to an attachment for an instrument, the arm comprising a plurality of joints whereby the configuration of the arm can be altered, the data anonymiser system comprising:

a receiver configured to receive a data stream captured by the surgical robotic system, the data stream comprising data relating to a surgical procedure and comprising personally-identifiable data;

a personally-identifiable feature detector configured to determine one or more personally-identifiable feature in the received data stream; and a data anonymiser configured to generate, in dependence on the determined personally-identifiable feature and the received data stream, an anonymised data stream omitting the personally-identifiable data.

The data stream may comprise one or more data channel from a group of data channels comprising: video data received from an endoscope coupled to the surgical robotic system; audio data recorded in respect of a surgical procedure; telematics data corresponding to the surgical robotic system; and state data comprising the state of at least a portion of the surgical robotic system. The personally-identifiable feature detector may be configured to determine the personally-identifiable feature in dependence on a first data channel of the group of data channels, and the data anonymiser may be configured to generate the anonymised data stream by modifying a second data channel of the group of data channels.

The data anonymiser may be configured to generate the anonymised data stream by one or more of: removing a data portion from the received data stream, the removed data portion comprising personally-identifiable data, and masking a data portion of the received data stream, the masked data portion comprising personally-identifiable data. The received data stream may comprise two or more data channels from the group of data channels, and the data anonymiser may be configured to generate the anonymised data stream by modifying the data portion in respect of at least two of the data channels separately.

According to another aspect of the present invention there is provided a data anonymiser for a robotic system configured to perform the method as described herein.

According to another aspect of the present invention there is provided a robotic system comprising a robot having a base and an arm extending from the base to an attachment for an instrument, and a data anonymiser configured for anonymising data by the method as described herein.

According to another aspect of the present invention there is provided a non-transitory computer readable storage medium having stored thereon computer readable instructions that, when executed at a computer system, cause the computer system to perform the method as described herein.

Any feature of any aspect above can be combined with any one or more other feature of any aspect above. Any method feature may be rewritten as an apparatus feature, and vice versa.

BRIEF DESCRIPTION OF THE DRAWINGS

The present invention will now be described by way of example with reference to the accompanying drawings.

In the drawings.

DETAILED DESCRIPTION

The following description is presented by way of example to enable a person skilled in the art to make and use the invention. The present invention is not limited to the embodiments described herein and various modifications to the disclosed embodiments will be apparent to those skilled in the art. Embodiments are described by way of example only.

Data, such as video data, captured during a surgical procedure can include information which can identify a patient, such as an image of a patient's face or other identifiable anatomy, or an image of the patient's name which might be written on a patient information sheet or whiteboard in the operating room. Patient privacy, and related ethical considerations, are of high concern to hospitals, and this limits the ways in which the captured data can be used. Anonymising the captured data means that restrictions put in place to guarantee patient privacy would not apply to the anonymised data (since patient privacy would be provided by the anonymisation). Thus a greater use can be made of the anonymised data, for example in offering teaching and training services to those outside the team that performed the surgical procedure, including to those in other hospitals.

Described herein are methods and apparatus for anonymising data in a surgical robotic system. Data captured by the surgical robotic system, for example data generated and/or recorded by the system as the procedure is performed, can be received at a data anonymiser system. The data anonymiser system can be part of the surgical robotic system or can be separately provided. A detector of the data anonymiser system is used to determine a personally-identifiable feature in the received data, for example to determine that such a feature is present, and the location or timing in the data that that feature is detected. A data anonymiser is then used to generate anonymised data using the received data and the detected feature. The anonymised data can comprise a copy of the received data which omits the personally-identifiable data, and/or it can comprise a modified version of the received data in which the personally-identifiable data is removed or otherwise obscured.

Figure 5:
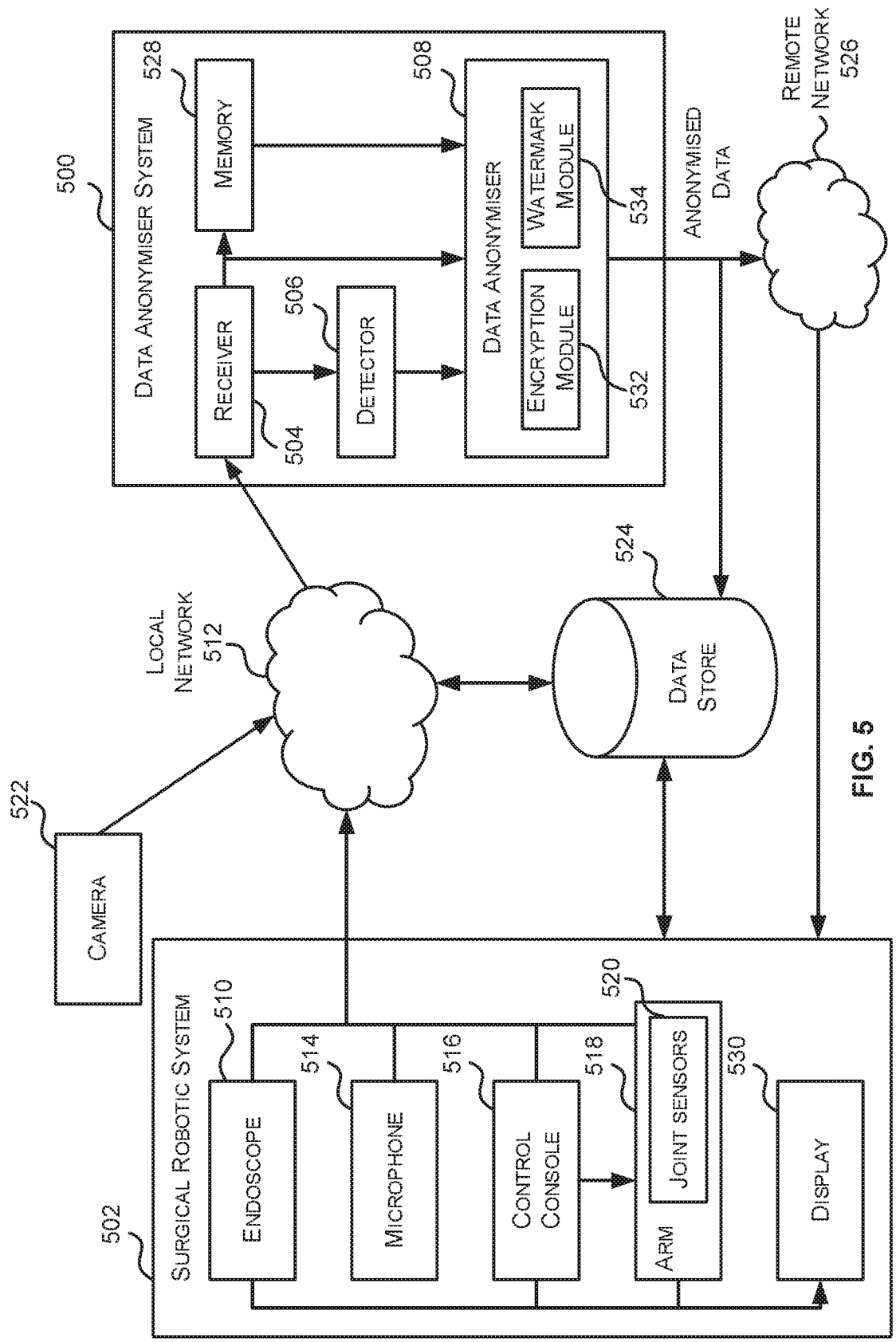
FIG. 5 is a block diagram of an example data anonymiser system.

Reference is first made to FIG. 5, which illustrates an example data anonymiser system 500 for automatically anonymising data relating to a surgical procedure performed by a surgical robotic system 502. The surgical robotic system comprises at least one surgical robot having a base and an arm extending from the base to an attachment for an instrument. The arm comprises a plurality of joints whereby the configuration of the arm can be altered. An example surgical robotic system 502 is described below with reference to FIG. 6.

The data anonymiser system 500 comprises a receiver 504, a detector 506 and a data anonymiser 508. One or more of the receiver 504, the detector 506 and the data anonymiser may be implemented by one or more computing-based devices, such as, but not limited to, the example computing-based device described herein with reference to FIG. 8. The receiver 504 is configured to receive a data stream comprising data relating to the surgical procedure. The receiver passes the received data stream to the detector 506 which is configured to determine a personally-identifiable feature in the data. The data anonymiser 508 is configured to generate, in dependence on the determined feature and the data stream, an anonymised data stream which does not include the personally-identifiable data. The generation of the anonymised data will be described in more detail below.

The data stream received by the receiver can comprise endoscopic video data, i.e. video or images captures by an endoscope 510. The receiver 504 is configured to receive the video data from the endoscope, for example via a local network 512. The local network can comprise one or more of an HDMI interface, an SDI interface, and other video interfaces. In some cases, the receiver can be configured to receive the video data from the endoscope via a direct coupling, which may comprise one or more of an HDMI interface, an SDI interface, and other video interfaces. The local network 512 is suitably on the hospital premises, so there is no restriction on transmitting personally-identifiable data over this local network. This video data is likely to include video or images of the operating room itself—captured by the endoscope before the endoscope tip is inserted through a port towards the surgical site. (The term 'port' can be considered to comprise a physical port and/or a virtual port—as described elsewhere herein.) The field of view of the endoscope whilst it is coupled to the arm can be well characterised and potentially controlled to avoid capturing sensitive data. On the other hand, the endoscope is likely to be operational, i.e. capturing video, whilst being manually held and mounted to the robot arm. Whilst manually held, the field of view is not well known, and could therefore inadvertently include personally-identifiable information. The video data may comprise an image or video of a patient's face or of the faces of operating room staff.

Where the patient's details are written down in the operating room, the video data may also comprise video of these details. Thus, the video data is likely to comprise personally-identifiable data relating to one or more of the patient undergoing the surgical procedure and a member of the operating room staff.

The data stream can also comprise audio data captured by a microphone 514 which optionally forms part of the surgical robotic system 502. The microphone can be located at or adjacent the robot arm, and/or at or adjacent a control console 516 of the surgical robotic system. In this way, the microphone can capture audio from the surgical procedure, including from operating room staff assisting in the surgical procedure, and from an operator of the control console such as a surgeon. The audio data may comprise discussions of the patient and so would thus comprise personally-identifiable data. The receiver 504 is configured to receive the audio data from the microphone, for example via the local network 512.

The data stream can also comprise telemetry/telematics data and/or state data. The state data can indicate the state of at least a portion of the surgical robotic system. The telematics data and/or state data can be produced by the control console 516 as it effects control of an arm 518 of the robot. The telematics data and/or state data can be produced by sensors on the arm itself such as joint sensors 520 of the arm which are configured to sense the configuration of each of the arm joints. Whilst it is perhaps less apparent that the telematics data and/or state data could comprise personally-identifiable data, it is possible for the way in which the arm is moved and/or located to identify a patient on which the arm is being used to perform a procedure, or the surgeon operating the arm. This may particularly be the case when such data is taken together with other data relating to the procedure, such as the video and/or audio data. The receiver 504 is configured to receive the telematics data and/or the state data from the surgical robotic system (e.g. from the control console and/or from the arm), for example via the local network 512.

Each of the video data, the audio data, the telematics data and the state data can be considered to be a separate data channel of the data relating to the procedure captured by the system. The data channels are suitably time-synchronised with one another. The data channels may be time-synchronised in any suitable manner that allows features or events of one data channel to be correlated to a particular time or period of time, and/or a particular feature or event in another data channel. For example, a plurality of the data channels may include, or be linked to, common timestamps or a common timeline.

Video data may be generated by the surgical robotic system 502 itself (e.g. video or images captured by the endoscope 510). Video data may also be captured by a camera 522 within the operating room which need not be part of the surgical robotic system 502, but it may be. The camera can be used to capture a view of the exterior of the surgical site, the surgical robotic system and/or the actions and interactions of the operating room staff. In some scenarios the field of view of such a camera will include a patient's face, i.e. personally-identifiable data. In some cases, such video data captured by a camera can also be anonymised using the present techniques. For example, the video data captured by the camera can be time synchronised with one of the data channels, and anonymised in dependence on the detection of a personally-identifiable feature in one or more data channel.

All or a portion of the telematics data and/or the state data may be generated by the surgical robotic system 502 itself (e.g. data relating to the position and/or movement of the surgical robot arm(s), instrument(s) attached thereto, and any hand controllers that control the movement of the robot arm(s)). Where the field of view of the camera 522 includes at least a portion of the arm, video data from the camera can be used to obtain or infer telematics/state data of the arm (e.g. by analysing the video generated by the camera). In this way, at least a portion of the data stream relating to the surgical procedure may be generated by one or more external source.

The receiver 504 may receive the data stream relating to the surgical procedure via any suitable means. For example, in some cases the surgical robotic system 502 and/or the camera 522 may provide the data to the receiver 504 via a wireless or wired communication connection 512 such as, but not limited to, an Ethernet connection, Wi-Fi® connection, Bluetooth® connection, Near-Field Communication (NFC) connection, HDMI connection, SDI connection, other video interface connections or the like. In these examples, all or a portion of the data may be provided to the receiver 504 in real time (or in substantially real time) while the surgical procedure is being performed.

In other cases, the data relating to the procedure may be captured by another device (e.g. a computing-based device) during the procedure and stored in a storage device 524 (e.g. a memory) and subsequently provided to the receiver 504 via a communication connection 512 or via any other suitable means. In some cases, all or a portion of the data may be stored, at the location at which the procedure is performed (e.g. the operating theatre), on a portable storage medium, such as, but not limited to a USB (universal serial bus) memory stick or SD card, and physically transported to the location of the receiver 504 where it is coupled to the receiver 504 so that the receiver 504 can read the data from the portable storage medium.

The detector 506 is configured to detect whether or not the data stream comprises a personally-identifiable feature, which can be indicative of the presence of personally-identifiable data in the data stream. Where a personally-identifiable feature is detected, the detector can determine the portion of the data stream which comprises the personally-identifiable data. This detection can be done in one of several ways. A first approach is to identify the portion of the data stream where there is (or may be) personally-identifiable data and to flag or mark that portion so that it can be removed (or not saved/transferred). This approach can involve performing image analysis on the endoscope video data to identify the portion of that data where (e.g.) a face is visible. That portion can be removed from the anonymised video data, retaining the remainder of the video data which can include other video from the operating room or operation.

A second approach is to identify a portion of the data stream where there is not personally-identifiable data (or where it is highly unlikely that there will be personally-identifiable data) and to flag or mark such a portion as 'safe' to be saved/transferred. To take an example, consider endoscope video. As the endoscope is attached to the robot arm, and before it is inserted through the port, it will capture video of the operating room (i.e. video from outside the surgical field). This video may comprise personally-identifiable data such as a patient's face. Once the endoscope is inserted through the port, it will capture video of the internal surgical site (i.e. video from inside the surgical field), which is highly unlikely to contain personally-identifiable data.

This will remain the case until the endoscope is retracted from the port (when the video will transition from being inside the surgical field to being outside the surgical field), when it will again begin to capture video of the operating room, potentially including personally-identifiable data. The 'safe' data can therefore comprise video captured between insertion of the endoscope through the port and retraction of the endoscope from the port, i.e. video of a target operative field, and suitably nothing else. This approach can thus involve determining when the endoscope is inserted through the port and when it is retracted from the port and removing or otherwise anonymising any portion of video data captured between these identified times, i.e. when the endoscope is not inserted through the port.

It will, of course, be understood that a combination of the first and second approaches can be used.

In response to determining the personally-identifiable feature in the data stream, the detector 506 may be configured to generate an output indicating one or more of:
that the personally-identifiable feature has been detected,
the type of feature detected,
the time of the feature (i.e. the time that that feature occurred),
the portion of the data stream to which the feature relates (such as part of a still or video image, or successive parts of a sequence of images, or more generally which of the data channels comprises the feature), and
the duration of the feature.

The output is provided to the data anonymiser 508.

The data anonymiser is configured to receive the output from the detector and to receive the data stream via any suitable means, for example from the receiver. The data anonymiser could also be configured to receive the data stream over the local network 512. The data anonymiser is configured to generate an anonymised data stream based on the received data stream and the determined personally-identifiable feature. The anonymised data can be saved to local or remote storage, such as to the storage device 524. The anonymised data can be transmitted over a remote network 526 such as the internet. The anonymised data can be transmitted by any suitable method, such as over a wired link or over a wireless connection to a local access point that connects to the remote network.

The anonymised data is generated by the data anonymiser 508 by omitting data identified by the personally-identifiable feature as comprising (or potentially comprising) personally-identifiable data. Such data can be omitted in several ways. One way in which the personal data can be omitted is by the data anonymiser saving the parts of the received data stream with the exception of those parts that are identified as comprising personal data. In this way, the parts of the received data stream comprising personal data can be removed from the received data stream. Thus, taking the first approach above, of flagging a portion of data comprising personally-identifiable information, the flagged portion can be removed from the data stream whilst saving/transferring the remainder of the data stream. Taking the second approach above, the data flagged as safe can be saved/transferred, whilst the remainder of the data stream is discarded, or not saved/transferred.

Another way in which the personal data can be omitted is by the data anonymiser blurring or otherwise masking a portion of the data corresponding to the personal data. For example, where a face is identified in a video sequence, each frame of the sequence in which the face is identified can be removed from the data. Alternatively, the part of the image identified as the face can be blurred or masked to obscure the face, whilst retaining the remainder of the frame of data. This has the advantage of not discarding more information than is needed to preserve privacy. Examples of masks that can be applied include a Gaussian blur mask, a constant-value mask (which can have the effect of applying a colour block over the part of the image—e.g. pixels of the face can be replaced by black pixels), and a random-value mask (which can have the effect of applying random pixel values to the part of the image to be obscured). Another example of a mask is one generated in dependence on a Generative Adversarial Network (GAN), which can be used to obtain a photorealistic face to mask a real face in the video. The photorealistic face obtained from the GAN may be generated by a system trained on many real faces. A further example of masking a data portion comprises downsampling the data portion. The downsampling can have the effect of decreasing the resolution of the data portion, which can 'mask' the original data.

Similarly, where the personally-identifiable feature is detected in the audio data channel, the data anonymiser can be configured to replace a portion of the received audio data with, for example, white noise or a single tone, or to remove that portion of the audio data when generating the anonymised data.

The data anonymiser system 500 may be remote from the surgical robotic system 502. For example, the surgical robotic system 502 may be located in an operating theatre and the data anonymiser system 500 may be in another room in the hospital or treatment centre. In other cases, the data anonymiser system can be integrated with the surgical robotic system, for example at the control console.

Suitably the data anonymiser system 500 is configured to process the data stream in real time (or in substantially real time). The data anonymiser system can comprise a memory 528 such as a buffer memory for temporarily storing the received data stream. The data anonymiser 508 can read the stored data stream from the memory 528. Processing the data stream in real time or in substantially real time enables the anonymised data to be transmitted over the remote network, also in real time (or in substantially real time). The anonymised data can be transmitted to a server located in the cloud, for example to an assistance module at the server. The assistance module can analyse the anonymised data to extract performance or other metrics and/or to generate advice or suggestions in response to the analysis. The advice can comprise advice relating to the next step to take in a particular procedure, how to most effectively perform a given step, suggestions relating to the procedure being performed or the step in the procedure being performed, and so on. This advice can be provided by the remote server, over the remote network 526, to the surgical robotic system 502, for example to a display 530. In this way, a surgeon operating the surgical robotic system can receive the advice/suggestions in real time (or in substantially real time) as they are performing the procedure on a patient.

In this way the data anonymiser system enables use of a remotely-based assistance module to enhance the procedure as it is being performed by the surgeon. In some cases, the anonymised data can be sent to a remotely-located person such as another surgeon. In this way, a more experienced surgeon can offer timely advice to a less experienced colleague without needing to be in the same location.

In some cases, the data stream, as received by the receiver, is presented to an operator (e.g. surgeon) of the surgical robotic system in real time, contemporaneously with generating the anonymised data stream. This can help avoid latency issues in the generation of the anonymised data from impacting the performance of the surgery.

Suitably the received data stream is modified before it is saved or transferred to a remote location, e.g. a location remote from the operating room (or hospital) at which the procedure is performed. That is, the data stream is anonymised before it is saved or transferred to the remote location. The data stream can be modified before it is saved to local storage, such as the storage device 524. The storage device can store both the unmodified data stream and the modified (anonymised) data stream.

Suitably, the operator of the surgical robotic system such as a surgeon, or another member of staff at the hospital, is able to control whether or not the data or modified data is saved and/or transferred. Thus, the data anonymiser system can present a user with an option to locally save the data stream. The data anonymiser system can present a user with an option to save and/or transfer the anonymised data stream, either to a local or to a remote location. In this way a user such as the surgeon or another member of hospital staff has oversight of how the data or anonymised data is used.

The data anonymiser system may comprise an encryption module 532, configured to encrypt at least a portion of one or both of the data stream and the modified data stream. The encryption module can be provided at or as part of the data anonymiser 508. The data anonymiser system may be configured to generate the anonymised data by encrypting a portion of data of the received data stream comprising personally-identifiable information. For example, the encryption module can encrypt each frame of a video where a face is detected, or only pixels of the detected face in each relevant frame, so that the face is not recognisable, e.g. because the system on which the video data is later replayed cannot decode the relevant frames or pixels. In some cases, the encryption module can be configured to encrypt portions of the received data stream that correspond to a configuration in which personally-identifiable information may be included in the data stream. Personally-identifiable information need not be detected in the data stream. For example, the encryption module can be configured to encrypt the received data (such as by encrypting the video channel of the received data, optionally together with additional data of the received data) when the endoscope is not inserted through the port. The encryption module can encrypt the data in any suitable manner, for example by using an encryption key.

Such anonymised data (e.g. encrypted data) can be transferred to a remote location, preserving patient privacy, but also permitting the use of a corresponding decryption key to decrypt the anonymised data, enabling the unmodified data to be retrieved by an authorised party. This can be a useful way of increasing the use of a single set of data, i.e. the encrypted anonymised data, which can be used both in a manner that preserves privacy (in the encrypted form, in which identifying data is omitted) and in a manner that enables the full data to be reviewed (in the decrypted form, in which an authorised party can view the identifying data). Such an approach can avoid the need to save both the original data stream and an anonymised data stream, but can provide the benefits of having both 'sets' of data available to the relevant party.

In some cases, different segments or chapters of the received data can be encrypted with different levels of encryption. For example, the data stream can be segmented based on one or more feature of the data stream (or more generally, information relating to the surgical procedure). In this way, the data stream can be segmented according to one or more of the configuration of the arm, the type of instrument attached and/or its operational state, the operational state of the robotic system, the stage in the procedure, the surgeon controlling the robot, and so on. Each stage, or a group of stages, of the procedure can be associated with a different access level. This can enable access to groups of segments of the data stream to be selectively provided to different groups of people. Thus, the encryption module can be configured to apply a first level of encryption to a first portion of the data stream (e.g. corresponding to a first segment or group of segments) and to apply a second level of encryption to a second portion of the data stream (e.g. corresponding to a second segment or group of segments). The second level of encryption can be higher than the first level, i.e. decryption to the first level decrypts only the first portion of the data stream, whilst decryption to the second level decrypts both the first and second portions of the data stream. More than two levels of encryption may be provided.

The data anonymiser system may comprise a watermark module 534, configured to add a 'watermark' to one or both of the received data stream and the anonymised data stream. The watermark module can be provided at or as part of the data anonymiser 508. The watermark can comprise a digital signature and/or fingerprint. The watermark may be added to the data in such a way that at least a portion of the watermark can be considered to be 'hidden', i.e. it is not necessarily apparent that a watermark (or the hidden portion of the watermark) has been added. This can reduce the risk of the watermark (or the hidden portion of the watermark) being deliberately removed by a third party. For example, the watermark module may be configured to apply the watermark by one or more of encoding the watermark in the least significant bits of data, encoding the watermark as part of carrying out a discrete cosine transformation in respect of the data (for example when compressing the data), encoding the watermark using wavelet transformation, encoding the watermark using spread spectrum techniques, encoding the watermark using frequency and/or temporal masking, and so on.

The watermark module may be configured to add the watermark when the data is anonymised. In other implementations, the watermark module can be configured to add a watermark to the anonymised data when it is to be transferred remotely. Thus the watermark module need not be provided as part of the data anonymiser system, but can be provided separately. For instance, the watermark module may have access to the anonymised data, such as by being coupled to the data store 524 at which the anonymised data is stored. When the anonymised data is to be sent remotely, the watermark module can be configured to add the watermark at that stage, prior to the transfer. Details relating to the intended recipient and/or intended use of the anonymised data can be included in the watermark.

The provision of the watermark module enables the data (e.g. the anonymised data transferred to a remote server) to be tracked and/or identified. For instance, the watermark can comprise an identification of one or more of the hospital at which the procedure was performed, the surgeon/surgical team who performed the procedure, the robotic system used to perform the procedure (which could be identified by a unique serial number of one or more of the control console, the robot arm(s) and the instrument(s)), the type of the procedure, the date/time at which the procedure was performed, the person responsible for authorising the release of the data, an expiry date of the released data, and so on. Any desirable metadata can be included in the watermark. The watermarked anonymised data can thereby be tracked back to the hospital at which the procedure was performed. Thus on review of the anonymised data, any conclusions or results of the review (which might be carried out without knowing the details contained in the watermark) can be fed back to the relevant hospital/surgical team.

The watermark can comprise an indication of the use for which the anonymised data has been released. For example, anonymised data for a particular procedure may be released for review of that procedure, but not authorised for teaching—which could for example be because that procedure remains experimental. The watermark module can be configured to add a watermark that indicates that the data can be used for review (perhaps for review by a selected recipient which can be an individual or a hospital), and details of the person/organisation to whom the data was released. Should that data later be found to be used by another individual, or for another use, the release channel and the original authorised use can be determined from the watermark. For these purposes it may be useful if such information is contained in a hidden portion of the watermark, so that it will not (or cannot) be deliberately removed.

In some cases, where the data stream is segmented, different watermarks can be applied to different segments or groups of segments. This can be done for several reasons, including because a different instrument was used (so the instrument ID in the watermark might be different), because a different surgeon performed that part of the procedure (so the surgeon ID in the watermark might be different), because a segment has been released for a different purpose to another segment (so the details relating to recipient/purpose of use and so on in the watermark might be different).

Where data is stored at the local data store 524 and/or a remote data store, such data can be retained for a given amount of time. Retention of data for a minimum amount of time may be needed to satisfy legal or regulatory requirements. Suitably the data is associated with a lifespan value, indicating the length of time for which the data will be retained, and/or an expiry date, indicating the date on which the data can be deleted. The system can be configured to automatically delete the data once the lifespan value or expiry date is reached. For example, a hospital may have a policy of retaining data from surgical robotic procedures for a certain number of days, say 7 days. The lifespan value can therefore be set at 7 days. Once 7 days have expired from the completion of the procedure, the data relating to that procedure can automatically be deleted from local and/or remote storage. Instead of automatically deleting the data, a user may receive a prompt to confirm deletion of the data.

In some cases, the data anonymiser system can be configured to automatically anonymise data once the lifespan value or expiry date is reached. In this way, where the data stream is retained without being anonymised, it may be available for a period of time corresponding to the lifespan value (or until the expiry date). During this time the full data is available for review, for example locally within the hospital at which the procedure was carried out. Such review may be by the surgeon and/or surgical team who carried out the procedure. Suitably the lifespan value/expiry date can be selected so that the full data is retained for a duration long enough that a standard post-procedure review can be carried out on the full data. For example, where it is hospital policy to perform such a review within 7 days of the procedure, the lifespan value can be set at 7 days. The data can then be anonymised automatically at the end of this period of time, to ensure that patient confidentiality is maintained, but that the anonymised data stream remains available for a longer period.

In some cases, the data stream may be associated with a first lifespan value (or first expiry date). This lifespan value can determine the length of time for which the full data remains available. At the end of this time period, the data may be anonymised by the data anonymiser system. The anonymised data (and optionally the data stream) may be associated with a second lifespan value (or second expiry date, later than the first expiry date). This second lifespan value can determine the length of time for which the anonymised data remains available. For example, the first lifespan can be selected to be 3 days, and the second lifespan can be selected to be 14 days. In this example, the full data can be saved for 3 days following the procedure. During this time the full data may be reviewed. After 3 days the data is automatically anonymised. The anonymised data is retained for a further 14 days, after which it is automatically deleted. Other time periods can be chosen as desired. The second lifespan value (second expiry date) can indicate that the anonymised data is never to be automatically deleted. Instead of the data being automatically anonymised/deleted, a user may be prompted to anonymise and/or delete the data, at the relevant stage. Such prompting can ensure that an authorised person remains responsible for the management of the data.

The full data will typically be retained locally. In some cases the anonymised data may be retained locally. In some cases the anonymised data will be retained remotely. Following anonymisation, the system can be configured to transfer the anonymised data to a remote store, and to delete the data from the local store. Thus, in such cases, the full data may be available locally for a predetermined period of time, following which the anonymised data may be available remotely for a further predetermined period of time.

In some cases, once a data stream has expired or reached the end of its lifespan, it may be anonymised automatically prior to deletion. In this way, any recovery of the deleted data would not reveal personally-identifiable information, but rather only the anonymised data. In some cases, the data stream or anonymised data stream may be watermarked (or further watermarked) prior to deletion. Suitably the watermark indicates that the data is to be deleted. Thus, if the deleted data is restored, it can be determined that that data was deliberately deleted. In some cases, a playback system for replaying the data can be configured to prevent the playback of data with a watermark indicating that that data was deleted (or was to be deleted).

Figure 1:
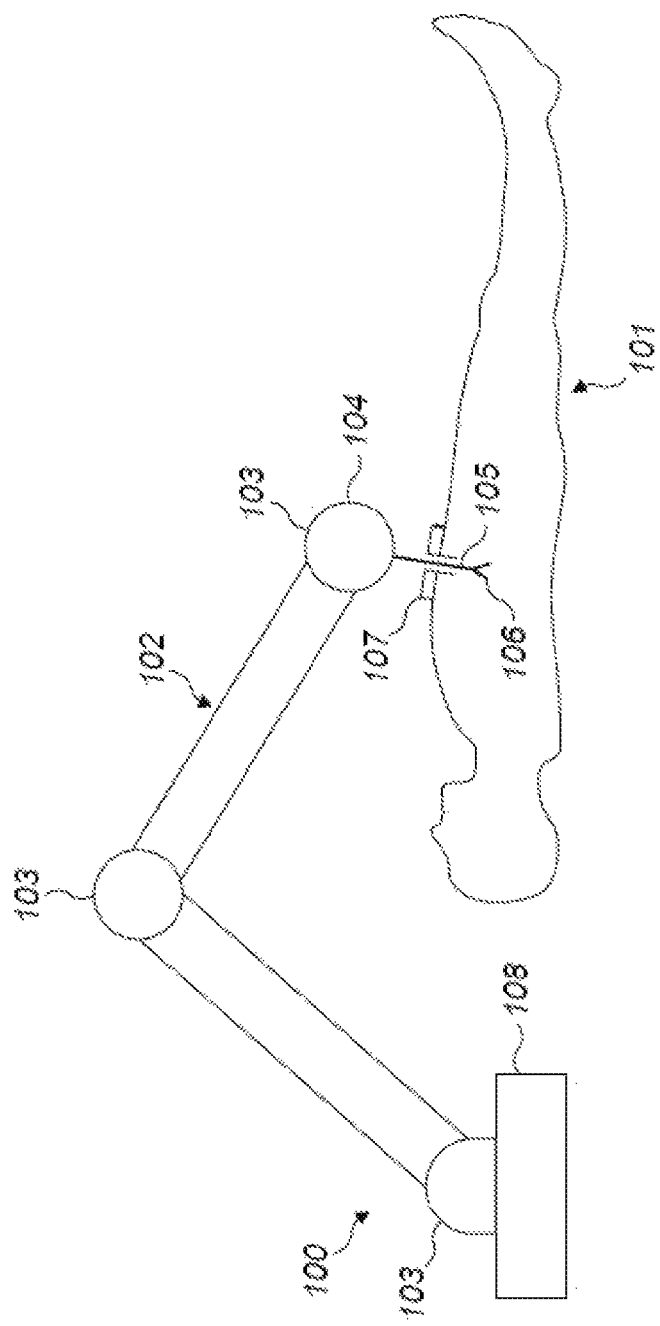
FIG. 1 schematically illustrates an example surgical robot performing an example surgical procedure.
Figure 2:
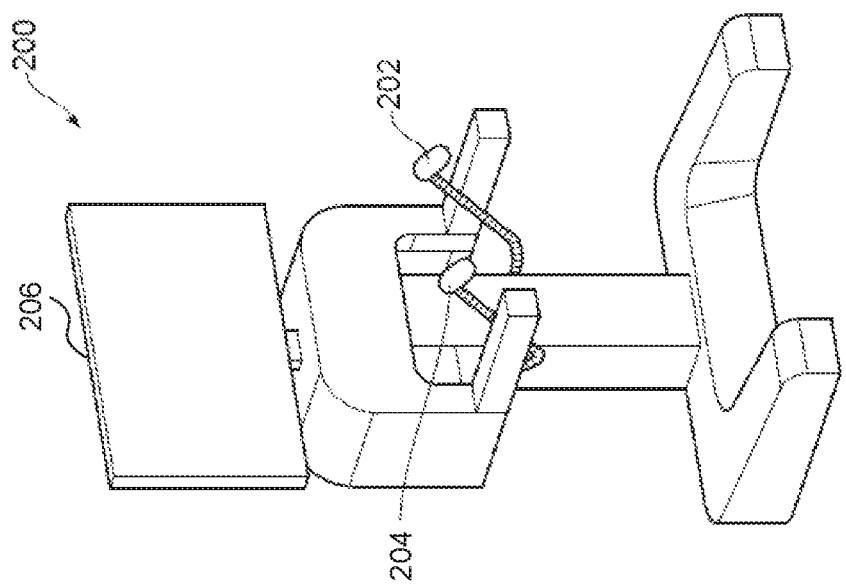
FIG. 2 schematically illustrates an example operator console.
Figure 3:
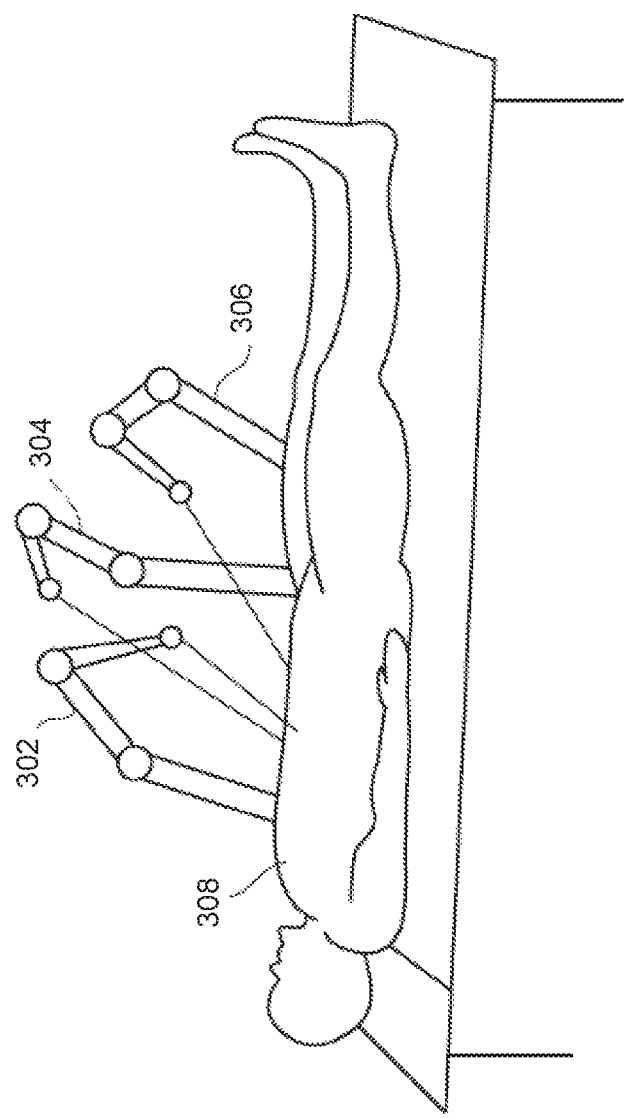
FIG. 3 schematically illustrates an example surgical robot system with a plurality of surgical robots.
Figure 6:
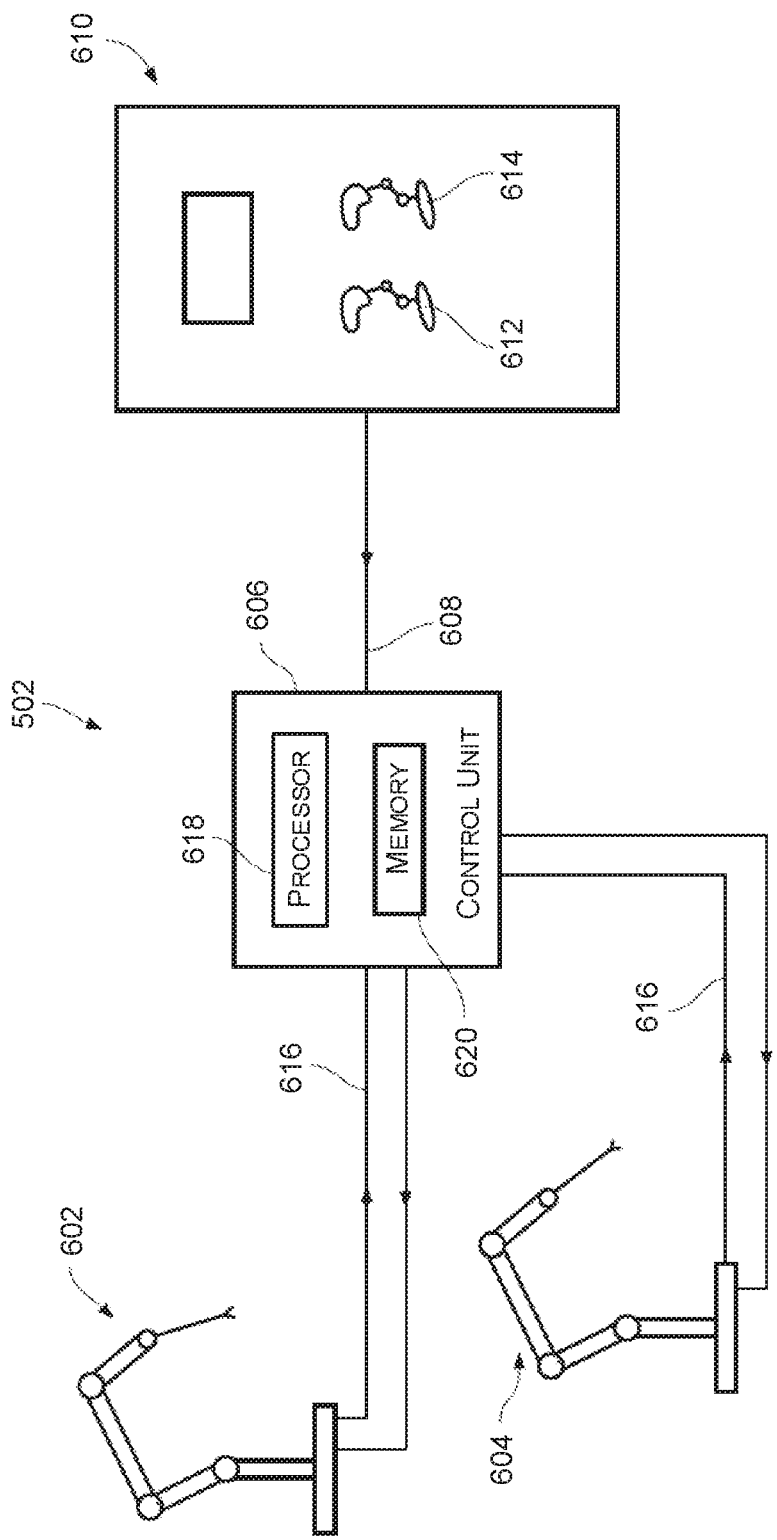
FIG. 6 schematically illustrates an example surgical robot system.

Reference is now made to FIG. 6 which illustrates an example surgical robotic system 502. In this example the surgical robotic system 502 comprises two surgical robots 602 and 604 driven by a control unit 606. The control unit 606 receives inputs 608 from an operator console 610 (such as, but not limited to the operator console 200 of FIG. 2), including inputs from first and second hand controllers 612, 614. The control unit 606 may receive other inputs from the operator console 610, such as foot pedal(s) inputs, voice recognition inputs, gesture recognition inputs, eye recognition inputs etc. The control unit 606 also receives inputs 616 from the surgical robots 602, 604. These inputs include sensor data from position sensors and torque sensors located on the robot arm joints. The control unit 606 may receive other inputs 616 from each robot, such as force feedback, data from or about the surgical instruments etc. The control unit 606 drives the robots 602, 604 in response to the inputs it receives from the robots 602, 604 and the operator console 610. The control unit 606 comprises one or more processors 618 and a memory 620. The memory 620 stores, in a non-transient way, software code that can be executed by the one or more processors 618 to control the drivers.

While the example surgical robotic system 502 of FIG. 6 comprises two surgical robots, it will be evident to a person of skill in the art that the methods and techniques described herein are equally applicable to surgical robotic systems with only one surgical robot and surgical robotic systems with more than two surgical robots.

The description above describes a patient's face detected in a video sequence as being an example of a personally-identifiable feature. In such a case, a feature in a given data channel (here the video data) can be determined and, in response, the data anonymiser can anonymise data in the same data channel (the video data). In some cases, one or more feature in one data channel can be determined and, in response, the data anonymiser can anonymise data in one or more other data channel as well as or instead of in the data channel in which the feature(s) was detected. It will be understood that many features other than face detection can prove useful in association with the present techniques. Some examples of features will now be described.

The personally-identifiable feature can be any feature in dependence on which the data stream can be characterised to comprise, or be likely to comprise, personally-identifiable information. This may be by detecting in the data stream personally-identifiable information such as a name or face, or by detecting configurations of the surgical robotic system or stages in the procedure at which it is likely that personally-identifiable information will be present in the data stream.

In some implementations, the personally-identifiable feature comprises, or is determined in dependence on, a state of the surgical robotic system. The state of the surgical robotic system (i.e. state data comprising the state of at least a portion of the system) can comprise one or more of:
 an attachment state of an instrument such as an endoscope,
 an operational state of an instrument attached to the arm,
 an operational state of the robot,
 a configuration of the arm and/or of an instrument attached to the arm, and
 a control state of the control console.

For example, where an instrument such as an endoscope is not attached to the arm, it is likely that personally-identifiable data will be present in the data stream (the endoscope field of view is likely to include the patient). Thus, the attachment state of the endoscope can be taken as a personally-identifiable feature in that it indicates the presence (e.g. when not connected to the arm) of personally-identifying information in the data stream. Thus, detecting the personally-identifiable feature, in this example that the endoscope is not attached to the arm, means that the video data captured by the endoscope in this state can be marked or otherwise indicated to be anonymised by the data anonymiser. In this example, the feature will be detected throughout the period in which the endoscope is unattached. The data stream may therefore be anonymised for the period in which the feature is determined to be present.

In some cases, the feature can comprise the attachment of the endoscope to the arm (i.e. the event of the attaching the endoscope, rather than a state in which the endoscope is/remains attached). Thus, in such cases, it need not be the case that the feature is always present for the data to be anonymised. In such cases, where the attachment of the endoscope to the arm is determined to occur, it will be known that the preceding data stream was captured whilst the endoscope was not attached to the arm. In response to the determination of such a feature, the data anonymiser can anonymise the data preceding the feature. Where an attachment event is preceded by a detachment event (i.e. the endoscope is detached from an arm before being reattached to the arm, or attached to another arm) both events can be determined to be features, in response to which the data anonymiser can be configured to anonymise the data stream between the features (occurrence of the events). In this way the data anonymiser can anonymise the video data for periods in which the endoscope is not attached to an arm.

The above case is an example of the data anonymiser anonymising one data channel in response to determining a feature in another data channel. Here, the feature is determined in the state data, and the video data is anonymised.

The operational state of an instrument can indicate whether a surgical tool is currently being controlled by a surgeon. For example, where a gripper tool is attached to the arm, the operational state of the tool can indicate whether the gripper tool is activated, i.e. is being moved/used by the surgeon. Since the tool will not be used by the surgeon unless they have a view of the surgical site, it can be determined that when at least one tool attached to an arm of the robot is under active control, that the endoscope will be capturing images of the surgical site and so will be located within a patient cavity. Thus, where a tool is in an operative state, such a feature can indicate that subsequent video data is 'safe', i.e. does not include personally-identifiable information. In response to the determination of such a feature, the data anonymiser can be configured to anonymise preceding data in the received data stream.

The operational state of the robot can be used to characterise or segment data in the data stream, for example by indicating whether or not an endoscope is inserted through a port. The operational state of the robot may comprise a mode of the robotic system, or of the control console. The robotic system can be initialised into, or put into, a 'port training' mode. In this mode, an instrument (which may be an endoscope or other type of instrument such as a gripper instrument) can be attached to the arm, and positioned partly within a port (the port can be a virtual port, i.e. need not be a physical port—this is discussed in more detail below). The arm can be moved by a user pushing on the arm to enable the system to determine the location of the port. In this way the system can establish a location of a virtual pivot point (VPP) about which an instrument is restricted to pivot when inserted through the port. The system can then be moved into an 'instrument adjust' mode in which the instrument can be further inserted through the port, towards a position in which surgical control of the instrument can begin. For example, where the instrument is an endoscope, the instrument can be inserted until the tip of the instrument (which can house the endoscope imaging device) is located adjacent a desired surgical site. In other cases, the instrument can be inserted until the end effector of that instrument is within the field of view of an endoscope located at the surgical site. The system can be moved between the instrument adjust mode and a 'surgical' mode in which control of the instruments can be effected by an operator (e.g. surgeon). The system can suitably also be moved between the surgical mode and an 'instrument change' mode in which an instrument can be removed and replaced. Where the system is in the surgical mode, it can be determined that the endoscope is inserted through a port. Thus, in some cases, the data stream can be indicated to be 'safe' where the system is in the surgical mode. At other times (when the system is in other modes) the data captured may comprise non-surgical data such as a view of the operating room, which might also include a view of the patient. Accordingly, the data anonymiser can anonymise data captured before the surgical mode is entered and/or data captured after the system has exited the surgical mode.

As mentioned, the port can comprise a virtual port. In some cases the port comprises a physical port through which an instrument can pass. In some cases, the port can be a 'virtual port'—a physical port need not be present. This can be the case where, for example, an instrument is to be inserted through a patient orifice, such as the patient's nostril or mouth. The virtual port can be defined in a manner analogous to that described above. For example, an instrument such as an endoscope can be at least partly inserted through the virtual port (e.g. into a patient's nostril) and the arm moved by a user to enable the system to determine the location in space of the virtual port. In this way the system can establish a location of a virtual pivot point (VPP) about which an instrument is restricted to pivot when inserted through the virtual port.

In some cases, the state of the surgical robotic system can comprise the configuration of the arm and/or of an instrument attached to the arm. This can provide information on how the instrument/arm is positioned, from which it can be determined whether it is likely that, for example, a procedure is being performed and/or the endoscope is inserted into the patient cavity.

The state of the surgical robotic system can comprise whether or not the virtual pivot point (VPP) for an instrument such as the endoscope is set. The setting of the VPP can indicate that the instrument is inserted through the port. The system can determine whether or not an instrument in inserted through the port based on knowledge of the location of the VPP and the location of the end effector and instrument shaft of the instrument (e.g. from arm kinematics). The state of the surgical robotic system can comprise the position and/or movement of an instrument or of a portion of the instrument, for example whether the tip of the instrument is inside a patient cavity or whether the tip has passed through a port or the defined VPP associated with that port.

In some cases an external source can indicate a state of the system. For example, a port may comprise an instrument sensor configured to sense when an instrument, or a particular part of an instrument, passes through the port. The instrument sensor may comprise a magnetic sensor configured to magnetically sense the instrument. For example the instrument sensor may comprise a Hall effect sensor. The instrument may be at least partially magnetic or magnetised. The instrument tip may comprise a magnet for sensing by the Hall effect sensor.

It will be understood that there can exist different ways of determining the same thing, e.g. whether the endoscope tip is inserted within a patient cavity. The data anonymiser can be configured to anonymise the data stream in dependence on any one, or any combination of, determined features. In this way, the data anonymiser system can operate with a redundancy, to better ensure patient privacy is protected even where a system fault might cause one feature to be inaccurately determined.

In some implementations, the personally-identifiable feature comprises, or is determined in dependence on, one or more of the following.

(i) Whether the Video Data Comprises a Circle that Grows or Shrinks.

As the endoscope passes through the port towards the surgical site, the port circumference will appear as a circle in the endoscope video that expands past the screen boundaries. As the endoscope is retracted from the port, the port circumference will appear as a circle in the endoscope video that contracts from beyond the screen boundary. The circle may leave the field of view of the endoscope to one side as the endoscope is moved away from the port. Thus, detecting, for example by image recognition, whether the video image comprises one or other (or both) of an expanding and a contracting circle can enable the detection of whether the endoscope tip passes inwardly or outwardly through the port (or both). Determination of this feature can therefore enable the data anonymiser to determine whether the endoscope tip is transitioning into or out of the surgical field. Thus this determination can enable the data anonymiser to generate the anonymised data accordingly. Data captured before endoscope insertion and/or after endoscope retraction can be anonymised. The data in between these events can be indicated to be 'safe' and not require anonymisation.

(ii) Whether the Video Data Comprises a Port-Identifying Feature.

The port can be marked with a visual indicator that can be detected by an image detection module. On detection of this visual indicator, it can be determined that the endoscope tip has passed through the port. The direction in which the endoscope has passed through the port can be determined based on how the visual indicator moves in the video data and/or on whether the prior state of the endoscope was 'inserted' or 'retracted'.

(iii) A Measure of One or More of Image White Balance, Image Spectrum, and Image Gradient from Centre to Edge of the Image, and/or a Change in a Measure of One or More of Image White Balance, Image Spectrum, and Image Gradient from Centre to Edge of the Image Video data captured from the surgical site is likely to be much redder than video data captured from the operating room. Video data captured from the surgical site is likely to have a greater image gradient from the centre to the edge than video data captured from the operating room. Thus one or more of these measures of the image (or of a series of images) can indicate whether the endoscope is inserted or not. In some cases, a change in the one or more measure, for example between frames in a sequence of video frames, can be used to determine that a transition has occurred. For example, where an earlier frame in a sequence has a lower red content than a later frame in the sequence, it can be determined that a transition from video of the operating room (outside the surgical field) to video of the patient cavity (inside the surgical field) has occurred.

The measure of the image spectrum may comprise a measure obtained within the visible spectrum, outside the visible spectrum, or both inside and outside the visible spectrum. For example the image spectrum may span the visible spectrum. Suitably the image spectrum comprises one or more of infrared and ultraviolet parts of the spectrum. The measure of the image spectrum may comprise a measure obtained across multiple bandwidths, such as two or more of a visible bandwidth, an ultraviolet bandwidth and an infrared bandwidth. In some cases, where there is a drop in the level of UV light between frames, it can be determined that a transition from the operating room (where there may be more/brighter UV sources) to the patient cavity has occurred. An increase in the level of IR light between frames may similarly indicate that a transition from operating room to patient cavity (where there may be relatively higher IR emission) has occurred.

The frames may be successive frames in the sequence, or they may be spaced apart by one or more other frames. A rough determination of the transition into the surgical field or out of the surgical field can be found by comparing frames that are spaced from one another temporally by, say, 30 seconds. Any other suitable time period can be used, as would be apparent to the skilled person. Once a transition occurring in a specified time period has been identified, then frames separated by a smaller time period can be compared. In some cases, frames can be compared at a series of successively smaller time separations. For example, 30 seconds, then 10 seconds, then 2 seconds, then 0.5 seconds. Greater and/or smaller time separation values can be used. More or fewer different time separations can be used. In this way, a finer determination can be iteratively achieved at lower processing cost and/or time.

The measure may comprise that a growing proportion of the image includes one or more of relatively redder light, relatively less UV light, relatively more IR light, and so on. This can indicate that the endoscope is approaching a port or patient cavity. In this way, the measure can be an indication that the captured video is transitioning from being outside the surgical field to being inside the surgical field. The converse may also be true: where the measure comprises that a shrinking proportion of the image includes one or more of relatively redder light, relatively less UV light, relatively more IR light, and so on, it can be determined that the endoscope is transitioning from being inside the surgical field to being outside the surgical field.

The measure may comprise a measure of the absorption of electromagnetic radiation in a given frequency band or bands. For example, a measure of the absorption, such as a differential absorption, can be used to detect patient tissue. This can indicate that the endoscope is within the patient cavity, or perhaps that the patient is visible in the field of view. The measure can be used with a different metric, such as a state of the system, to identify the tissue being viewed (optionally including whether the identified tissue is internal or external).

The measure of the image white balance, image spectrum and/or image gradient may comprise an average value for the image.

(iv) Whether the Video Data Comprises an Anatomical Feature.

The video data can be analysed to determine objects shown within the video data. Where, for example, internal anatomy such as a blood vessel or internal organ is detected, the system can determine that the endoscope is inside the surgical field. The data anonymiser can selectively anonymise parts of the video data that are not defined as being captured within the surgical field. Thus, where a video segment comprises an image of an internal organ, the video segment can be marked as 'safe' and anonymisation may not need to occur. A further check may be made to ensure that the organ identified is indeed internal to the patient at the time, for example by also considering a measure of the image spectrum.

An anatomical feature may be detected that is indicative of the endoscope being outside the surgical field. For example, an analysis of the video data may determine that the video data comprises an external view of a patient's abdomen, or arm. In such cases, the relevant portion of the video data may be marked as 'safe' if it can be determined that no personally-identifiable data is visible (for example where the abdomen occupies the whole field of view), or not marked as 'safe' (which can include being marked as 'not safe') where potentially personally-identifiable information may be present (such as a distinctive tattoo on an arm).

(v) Whether the Video Data Comprises an Object Known to be External to the Surgical Field.

Where video data analysis determines that an object in the operating room (such as an operating table, a robotic arm, a heart-rate monitor and so on) is visible, it can be determined that the endoscope is outside the surgical field and is capturing video from the operating room itself. Since this might include personally-identifiable information, such a portion of the video data may be marked for anonymisation. In some cases, the video data can be marked as 'safe' where it can be determined that no personally-identifiable information is visible, for example where a known 'safe' object (e.g. legs of an operating table) occupies the whole field of view.

(vi) The Procedure being Performed.

For different procedures, the video forming the video data is likely to comprise different characteristics. For instance, the number of times in the procedure that the endoscope is inserted/removed from the port, the duration of the periods of insertion, the surgical site visible during inserted periods, and so on. Basing the determination of the feature on the procedure being performed can enable video analysis of the video data to know what to expect, or roughly what to expect. This, in turn, can enable detection of features in the video with a higher accuracy.

(vii) A Machine Learning System that has been Trained Using One or More Known Features.

An operator can indicate to the system when a feature is present in the data stream, and this indication can be passed to a machine learning system that can learn from the input indication so as to be able to recognise the same or similar features in other data. The machine learning system may comprise a convolutional neural network. The machine learning system may comprise a recurrent neural network.

The personally-identifiable feature may, in some cases, comprise a marker associated with the data stream. The marker may form part of the data stream, for example the marker may have been added to the data stream during the procedure or at some point afterwards. One or more data channel of the data stream may comprise the marker. For example, the video data can comprise the marker. The marker may take any suitable form, which may be dependent on the data channel with which the marker is associated or of which the marker forms a part. In some cases, the marker may be an augmentation added to the video stream. The augmentation may be added as the video is captured or at some point after the video is captured. The marker can indicate the presence of one or more other feature described herein (such as the stage in a procedure, the visibility of an internal organ, the state of the system and so on). The marker can indicate a state or transition towards, away from or between other such features described herein (such as whether the video is captured inside a surgical field, outside a surgical field, and so on).

Combinations of these features may usefully be used. For example, detecting that a circle expands in the image, followed by an increase in the redness of the image, can be used to determine that the endoscope tip has been inserted through the port. Combinations of features may advantageously increase the accuracy with which such determinations can be made.

In some implementations, the endoscope may have an angled tip. In such cases, the orientation of the tip can be controlled before the endoscope is retracted from the patient cavity so that the field of view of the endoscope is restricted to a non-sensitive patient section, i.e. avoiding the face and possibly also any other potentially-identifiable anatomy. This can reduce the amount of data in the data stream requiring anonymisation. Accordingly, the time to process (anonymise) the data can be reduced.

Figure 4:
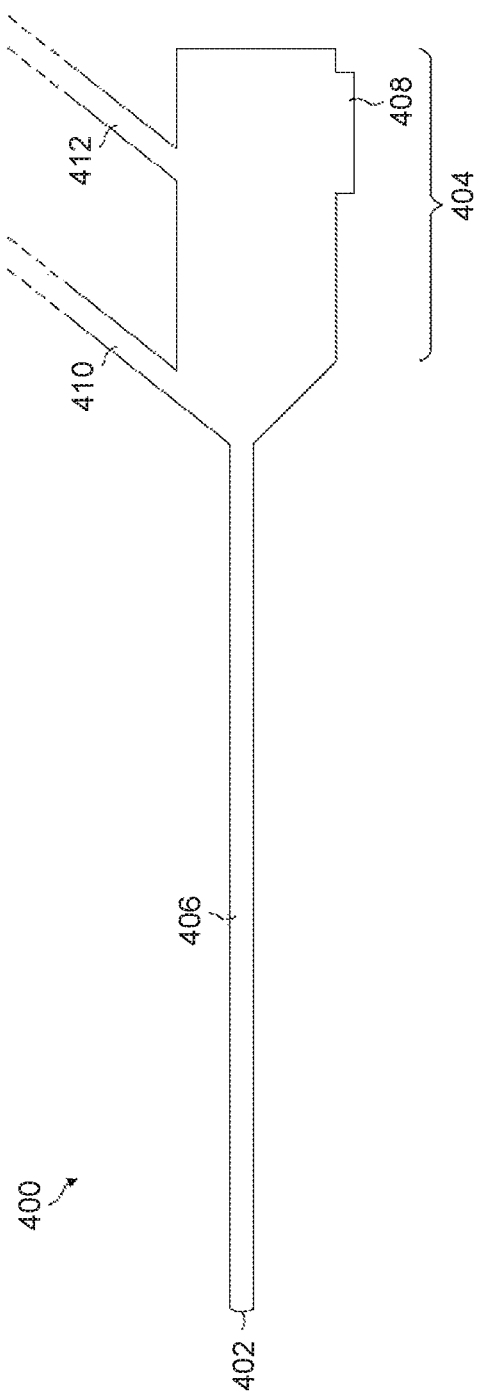
FIG. 4 schematically illustrates an example endoscope that is attachable to a surgical robot arm.

An example endoscope has been described above with respect to FIG. 4. Other types of endoscope can be used with the present techniques. Such endoscopes includes a "chip-on-tip" type endoscope, where the endoscope can be considered to be a probe at the end of which a camera can be mounted. The camera may take the form of a chip, for example a CCD chip, and optionally some associated processing logic (at least some processing logic may be provided separately). The endoscope described with reference to FIG. 4 operates with an external light source. It is also possible to use endoscopes that operate with an internal light source. For example, a light source might be provided as part of the endoscope itself, and light routed to a desired light output location. The light routing can be achieved by one or more fibre optic cable. In some cases, a light source can be provided at or adjacent a tip of the endoscope. Such a light source may comprise an LED. Multiple LEDs can be provided. The light source, whether internal, external, or some combination of internal and external can be controlled so as to vary the intensity of light output and/or the frequency of light output.

In some cases, the endoscope can be provided with a light source (or more generally an illumination source) configured to output light (or more generally, electromagnetic radiation) outside the visible range. Suitably the illumination source is configured to output electromagnetic radiation across a spectrum. The spectrum may comprise one or more of visible light, ultraviolet light and infrared light.

As discussed above, anonymising the data can comprise removing a time slice from the data stream, or blurring/masking at least a portion of the data stream. Suitably the anonymisation of the data is performed on all the data channels, though it need not be. The anonymisation of the data can be performed on all the data channels at once, though it need not be. In some cases, the data anonymiser can be configured to anonymise a subset of the data channels. For instance, the data anonymiser can anonymise the video data channel, and possibly also the audio data channel, but need not anonymise the telematics data and/or the state data. This can be because the video data and possibly also the audio data is more likely to comprise personally-identifiable information.

Where the data anonymiser is configured to anonymise the data channels separately, the data anonymiser system is suitably configured to combine the anonymised data channel(s) with any remaining data channel(s) into the anonymised data stream before saving or transferring the anonymised data stream. In some cases, the data channels may be saved and/or transferred separately, or in a group comprising a subset of the data channels.

In some cases, as discussed above, the data anonymiser can modify a period of the received data stream (chronologically) before a detected feature, (chronologically) after a detected feature or (chronologically) between detected features. In some cases, the data anonymiser can be configured to anonymise the received data stream for a time period located about (i.e. to either side of) the detected feature. For example, the data anonymiser can be configured to anonymise the received data stream for a time period of 30 seconds before and 30 seconds after the feature is detected. The time period before the feature for which the data is anonymised need not be the same as the time period after the feature for which the data is anonymised.

The data anonymiser system may be used to anonymise the data stream in more than one way. In some cases, the data stream can be anonymised to a first level to generate first anonymised data, and anonymised to a second level to generate second anonymised data. In some cases the data anonymiser system is configured to generate the second anonymised data by further anonymising the first anonymised data. In some cases the data anonymiser system is configured to generate the second anonymised data by anonymising the data stream to a greater extent than the first anonymised data. For instance, the first anonymised data may have been anonymised by omitting faces from the received data stream (whether by completely removing the relevant portion of video data or masking the relevant portion of video data). The second anonymised data may have been anonymised by omitting all video data captured from outside the surgical field. In this way, the second anonymised data can be considered to be anonymised to a different (greater) level of anonymity than the first anonymised data.

Anonymised data that has been anonymised to different levels of anonymity can be used for different purposes. Referring to the example above, the first anonymised data may be provided to the surgical team for review. It is useful for the surgical team to review the actions of those in the operating room at the time of the procedure, as well as to review the procedure viewed at the surgical site. The second anonymised data may be provided to an academic department for review, and the academic department may only need access to the operations at the surgical site for the purposes of their review.

The data anonymiser may be configured to modify the data stream by converting known shapes to wire frame models and saving those models in place of the full data (i.e. removing the full data) in the data stream. This relates in particular to video data. Images of internal organs and/or of instruments and end effectors visible in the video data can be replaced by wire frame models of those organs, instruments or end effectors. Where a patient may be identified by a particular feature of an organ, such a modification of the data stream may assist in anonymising the data stream.

Figure 7:
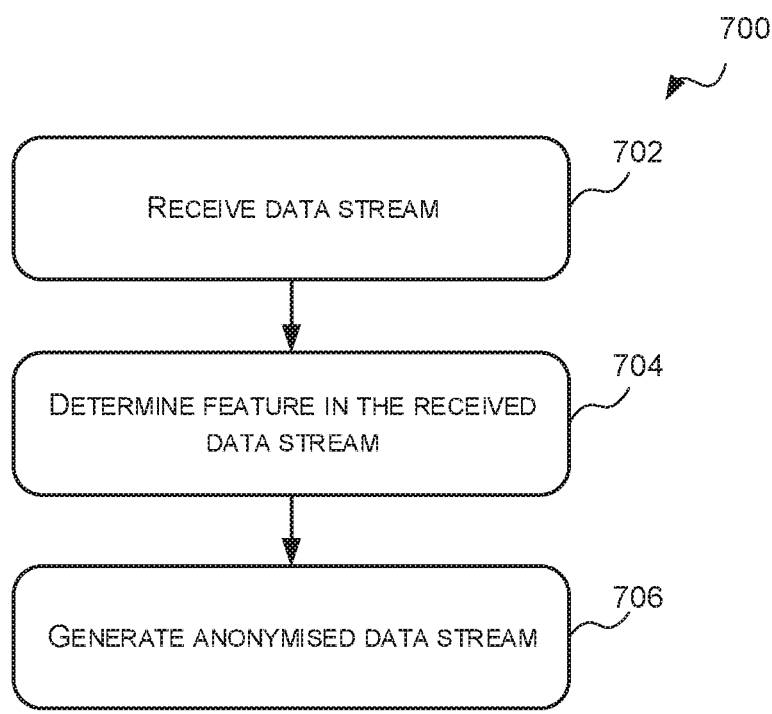
FIG. 7 is a block diagram of an example method of anonymising a data stream.

Reference is now made to FIG. 7 which illustrates an example method 700 for automatically generating an anonymised data stream based on a data stream captured by the surgical robotic system. At block 702, the data stream captured by the system is received. The data stream can be received by the data anonymiser system 500 discussed above, for example by the receiver 504. At block 704, a feature in the received data stream is determined. This can be a determination of a personally-identifiable feature, for use in anonymising the received data stream. For instance, the feature can be a determination that an endoscope has been inserted within a patient cavity. At block 706, an anonymised data stream is generated. The anonymised data stream is generated in dependence on the data stream received at block 702 and the feature determined at block 704.

In some cases, the video data need not be captured by an endoscope that is attachable to the surgical robotic system. For example, video data may be captured by an endoscope that is not a robotic endoscope. The endoscope may be a manually controllable endoscope. In this way, the video data, or more generally the data stream, may be captured by a device that is external to (not part of) the surgical robotic system. Such a device is not limited to an endoscope. Such a device may comprise a monitoring device for monitoring a patient and/or the status of a patient. Such a device can comprise one or more of an endoscope, a heart rate monitor, a blood pressure monitor, a blood flow monitor, a breathing monitor and so on.

A data anonymiser system may be provided for anonymising a data stream captured from a device such as a monitoring device. The data stream may comprise personally-identifiable data. For example, the data stream may comprise video data. The data anonymiser system is suitably configured to receive the data stream, determine a feature of the data stream indicative of personally-identifiable data, and generate, in dependence on the determined feature and the received data stream, an anonymised data stream omitting personally-identifiable data.

The data anonymiser system may comprise a receiver configured to receive the data stream. The data anonymiser system may comprise a data anonymiser configured to generate the anonymised data stream. The data anonymiser may be configured to determine the feature. Determining the feature may comprise detecting the feature in the received data stream.

The device may comprise an imaging device for imaging inside a surgical field. The device may comprise an imaging device for imaging at a surgical site within a patient. The data stream may comprise data captured from inside the surgical field. The data stream may comprise data captured from the surgical site within the patient. The data stream may comprise video data. The data stream may comprise data captured from outside the surgical field.

The device may be remote from (external to) a surgical robotic system. The data anonymiser can be for use in or with a surgical robotic system. The data anonymiser can form part of the surgical robotic system. The data may be captured from the device external to (or remote from) the surgical robotic system and anonymised at the surgical robotic system. That is, the surgical robotic system (or at least a portion of the surgical robotic system, such as a data anonymiser system) may be used to anonymise data captured remotely from the system. The data captured remotely from the surgical robotic system may be synchronised with data captured by the surgical robotic system. The data captured remotely from the surgical robotic system may be anonymised in dependence on the data captured by the surgical robotic system.

The feature of the data stream indicative of personally-identifiable data may comprise or be determined in dependence on a feature as described elsewhere herein (full details are not repeated here for brevity). For example, the feature of the data stream may comprise an indication that video data is captured from outside or inside a surgical field, and/or that the video data comprises a transition between being captured from outside a surgical field to/from being captured inside a surgical field. Such a feature may comprise (as described in more detail elsewhere herein) one or more of (including combinations of):
  whether the video data comprises a circle that grows or shrinks,
  whether the video data comprises a port-identifying feature,
  a measure of one or more of image white balance, image spectrum, and image gradient from centre to edge of the image, and/or a change in a measure of one or more of image white balance, image spectrum, and image gradient from centre to edge of the image,
  whether the video data comprises an anatomical feature,
  whether the video data comprises an object known to be external to the surgical field,
  the procedure being performed, and
  a machine learning system that has been trained using one or more known features.

The data stream may be anonymised as described elsewhere herein (full details are not repeated here for brevity).

In this way, it is possible to anonymise data captured remotely from a surgical robotic system, for example using the surgical robotic system. The data captured remotely from the surgical robotic system can be anonymised before it leaves the operating room.

Further processing of the data captured remotely from the surgical robotic system and/or the anonymised data can be performed, as described elsewhere herein, including encryption, watermarking, associating with lifespan values and so on.

Figure 8:
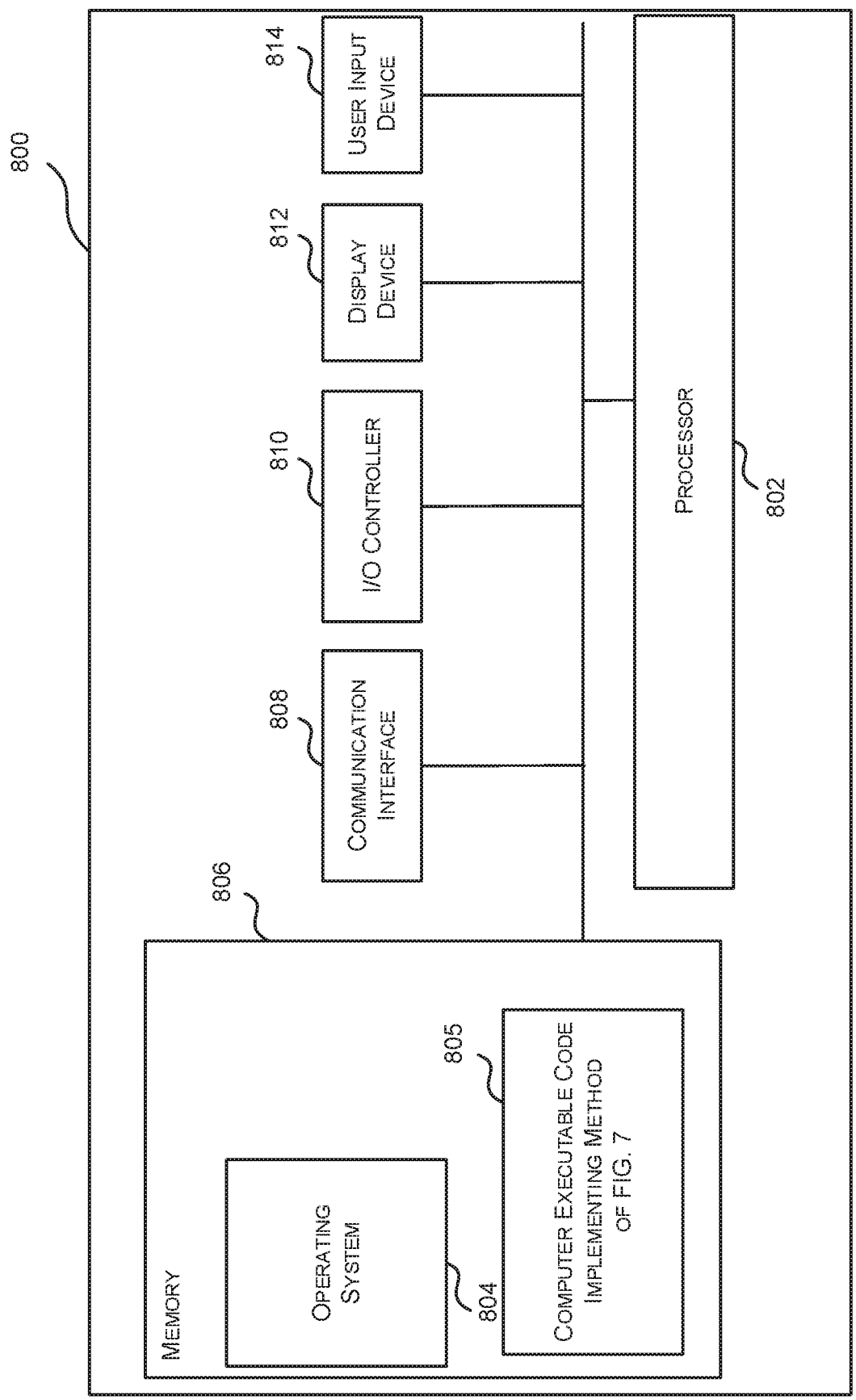
FIG. 8 is a block diagram of an example computing-based device.

Reference is now made to FIG. 8 which illustrates various components of an exemplary computing-based device 800 which may be implemented as any form of a computing and/or electronic device, and in which embodiments of the methods and augmentation systems described herein may be implemented. The computing-based device 800 comprises one or more processor 802 which may be microprocessors, controllers or any other suitable type of processors for processing computer executable instructions. In some examples, for example where a system on a chip architecture is used, the processors 802 may include one or more fixed function blocks (also referred to as accelerators) which implement a part of the method of modifying a data stream in hardware (rather than software or firmware). Platform software comprising an operating system 804 or any other suitable platform software may be provided at the computing-based device to enable application software, such as software 805 implementing the method of FIG. 7, to be executed on the device.

The computer executable instructions may be provided using any computer-readable media that is accessible by computing-based device 800. Computer-readable media may include, for example, computer storage media such as memory 806 and communications media. Computer storage media (i.e. non-transitory machine-readable media), such as memory 806, includes volatile and non-volatile, removable and non-removable media implemented in any method or technology for storage of information such as computer readable instructions, data structures, program modules or other data. Computer storage media includes, but is not limited to, RAM, ROM, EPROM, EEPROM, flash memory or other memory technology, CD-ROM, digital versatile disks (DVD) or other optical storage, magnetic cassettes, magnetic tape, magnetic disk storage or other magnetic storage devices, or any other non-transmission medium that can be used to store information for access by a computing-based device. In contrast, communication media may embody computer readable instructions, data structures, program modules, or other data in a modulated data signal, such as a carrier wave, or other transport mechanism. As defined herein, computer storage media does not include communication media. Although the computer storage media (i.e. non-transitory machine-readable media, e.g. memory 806) is shown within the computing-based device 800 it will be appreciated that the storage may be distributed or located remotely and accessed via a network or other communication link (e.g. using communication interface 808).

The computing-based device 800 also comprises an input/output controller 810 arranged to output display information to a display device 812 which may be separate from or integral to the computing-based device 800. The display information may provide a graphical user interface. The input/output controller 810 is also arranged to receive and process input from one or more devices, such as a user input device 814 (e.g. a mouse or a keyboard). This user input may be used to initiate verification. In an embodiment the display device 812 may also act as the user input device 814 if it is a touch sensitive display device. The input/output controller 810 may also output data to devices other than the display device, e.g. a locally connected printing device (not shown). In the description above actions taken by the system have been split into functional blocks or modules for ease of explanation. In practice, two or more of these blocks could be architecturally combined. The functions could also be split into different functional blocks.

The present techniques have been described in the context of surgical robotic systems, though at least some features described are not limited to such systems, but may be applied to robotic systems more generally. In some examples, the present techniques may be applied to robotic systems that operate remotely. Some examples of situations in which the present techniques may be useful include those that make use of 'snake-like' robots for exploration, investigation or repair. In the case of a surgical robot the end effector could be a surgical tool such as a scalpel, surgical cutter, surgical pincer or cauteriser. Robotic systems can include manufacturing systems, such as vehicle manufacturing systems, parts handling systems, laboratory systems, and manipulators such as for hazardous materials or surgical manipulators.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A method of anonymising data in a surgical robotic system, the surgical robotic system comprising a robot having a base and an arm extending from the base to an attachment for an instrument, the arm comprising a plurality of joints whereby the configuration of the arm can be altered, the method comprising:
receiving a data stream captured by the surgical robotic system, the data stream comprising data relating to a surgical procedure and comprising personally-identifiable data;
determining one or more personally-identifiable feature in the received data stream in dependence on a state of the surgical robotic system, wherein the personally-identifiable feature is determined in response to one or more of:
determining that an instrument is not attached to the arm,
a control input received from the control console, determining a change in a mode of the robotic system that modifies the operational coupling between a control console and at least one surgical instrument other than the endoscope, and a mode of the robotic system, the mode of the robotic system being one of a group of modes of the robotic system comprising a surgical mode in which robotic control of the instrument by an operator is enabled and a non-surgical mode in which robotic control of the instrument by the operator is not enabled; and
generating, in dependence on the determined personally-identifiable feature and the received data stream, an anonymised data stream omitting the personally-identifiable data, wherein generating the anonymised data stream comprises, in dependence on the determined personally-identifiable feature, one or more of:
removing a data portion from the received data stream, the removed data portion comprising personally-identifiable data, and
masking a data portion of the received data stream, the masked data portion comprising personally-identifiable data.

2. The method according to claim 1, in which the data stream comprises one or more data channel from a group of data channels comprising:
video data received from an endoscope coupled to the surgical robotic system;
audio data recorded in respect of a surgical procedure;
telematics data corresponding to the surgical robotic system; and
state data comprising the state of at least a portion of the surgical robotic system.

3. The method according to claim 2, in which the personally-identifiable feature is determined in dependence on the one or more data channel.

4. The method according to claim 2, in which the personally-identifiable feature is determined in dependence on a first data channel of the group of data channels, and generating the anonymised data stream comprises modifying at least one of a second data channel of the group of data channels, and the first data channel.

5. The method according to claim 1, in which masking the data portion comprises one or more of:
blurring the data portion; and
replacing values of data in the data portion with mask values.

6. The method according to claim 1, in which the data portion comprises one or more partial frames of data and/or one or more frames of data.

7. The method according to claim 1, in which generating the anonymised data stream comprises saving a subset of the received data stream; and/or the anonymised data stream is generated as the surgical procedure is being performed.

8. The method according to claim 1, in which the personally-identifiable feature is further determined in dependence on one or more of:
an operational state of the robot other than an indication of whether or not the endoscope is inserted through the port,
an attachment state of an instrument used to capture at least a portion of the data stream, where the instrument is not an endoscope,
analysis of data captured by an endoscope to determine whether or not the endoscope is inserted through a port,
a configuration of the arm,
an operational state of an instrument attached to the arm, and
a configuration of an instrument attached to the arm.

9. The method according to claim 1, in which the personally-identifiable feature is determined in dependence on one or more of:

an instrument sensor signal received from an instrument sensor, the instrument sensor being configured to detect an instrument passing through a port providing access to a surgical site;
whether the video data comprises a circle that grows or shrinks;
whether the video data comprises a port-identifying feature;
whether the video data comprises an image of a face;
a measure of image white balance;
a measure of image spectrum;
a measure of image gradient from centre to edge;
a procedure being performed;
a marker forming part of the data stream; and
a machine learning algorithm that has been trained using a plurality of known personally-identifiable features.

10. The method according to claim 1, in which generating the anonymised data stream comprises modifying the data portion for a time period that is one of:
before the personally-identifiable feature is determined,
after the personally-identifiable feature is determined,
both before and after the personally-identifiable feature is determined, and
between two personally-identifiable features.

11. The method according to claim 1, in which the method comprises:
generating the anonymised data stream in real time or substantially real time;
sending the anonymised data stream to a remote processor thereby enabling the remote processor to perform real time or substantially real time analysis of the anonymised data stream; and
receiving from the remote processor in real time or substantially real time the result of the analysis for assisting an operator of the surgical robotic system.

12. A data anonymiser system for a surgical robotic system for anonymising data from the surgical robotic system, the surgical robotic system comprising a robot having a base and an arm extending from the base to an attachment for an instrument, the arm comprising a plurality of joints whereby the configuration of the arm can be altered, the data anonymiser system comprising:
a receiver configured to receive a data stream captured by the surgical robotic system, the data stream comprising data relating to a surgical procedure and comprising personally-identifiable data;
a personally-identifiable feature detector configured to determine one or more personally-identifiable feature in the received data stream in dependence on a state of the surgical robotic system, wherein the personally-identifiable feature is determined in response to one or more of:
determining that an instrument is not attached to the arm,
a control input received from the control console,
determining a change in a mode of the robotic system that modifies the operational coupling between a control console and at least one surgical instrument other than the endoscope, and
a mode of the robotic system, the mode of the robotic system being one of a group of modes of the robotic system comprising a surgical mode in which robotic control of the instrument by an operator is enabled and a non-surgical mode in which robotic control of the instrument by the operator is not enabled; and
a data anonymiser configured to generate, in dependence on the determined personally-identifiable feature and the received data stream, an anonymised data stream omitting the personally-identifiable data, wherein the data anonymiser is configured to generate the anonymised data stream by one or more of:
removing a data portion from the received data stream, the removed data portion comprising personally-identifiable data, and
masking a data portion of the received data stream, the masked data portion comprising personally-identifiable data.

13. The data anonymiser system according to claim 12, in which the data stream comprises one or more data channel from a group of data channels comprising:
video data received from an endoscope coupled to the surgical robotic system;
audio data recorded in respect of a surgical procedure;
telematics data corresponding to the surgical robotic system; and
state data comprising the state of at least a portion of the surgical robotic system.

14. The data anonymiser system according to claim 13, in which the personally-identifiable feature detector is configured to determine the personally-identifiable feature in dependence on a first data channel of the group of data channels, and the data anonymiser is configured to generate the anonymised data stream by modifying at least one of a second data channel of the group of data channels, and the first data channel.

15. The data anonymiser system according to claim 12, in which the data anonymiser is configured to generate the anonymised data stream by one or more of:
removing a data portion from the received data stream, the removed data portion comprising personally-identifiable data, and
masking a data portion of the received data stream, the masked data portion comprising personally-identifiable data.

16. The data anonymiser system according to claim 15, in which the received data stream comprises two or more data channels from the group of data channels, and the data anonymiser is configured to generate the anonymised data stream by modifying the data portion in respect of at least two of the data channels separately.

17. A non-transitory computer readable storage medium having stored thereon computer readable instructions that, when executed at a computer system, cause the computer system to perform a method of anonymising data in a surgical robotic system, the surgical robotic system comprising a robot having a base and an arm extending from the base to an attachment for an instrument, the arm comprising a plurality of joints whereby the configuration of the arm can be altered, the method comprising:
receiving a data stream captured by the surgical robotic system, the data stream comprising data relating to a surgical procedure and comprising personally-identifiable data;
determining one or more personally-identifiable feature in the received data stream in dependence on a state of the surgical robotic system, wherein the personally-identifiable feature is determined in response to one or more of:
determining that an instrument is not attached to the arm,
a control input received from the control console,
determining a change in a mode of the robotic system that modifies the operational coupling between a control console and at least one surgical instrument other than the endoscope, and a mode of the robotic system, the mode of the robotic system being one of a group of modes of the robotic system comprising a surgical mode in which robotic control of the instrument by an operator is enabled and a non-surgical mode in which robotic control of the instrument by the operator is not enabled; and generating, in dependence on the determined personally-identifiable feature and the received data stream, an anonymised data stream omitting the personally-identifiable data, wherein generating the anonymised data stream comprises, in dependence on the determined personally-identifiable feature, one or more of:

removing a data portion from the received data stream, the removed data portion comprising personally-identifiable data, and masking a data portion of the received data stream, the masked data portion comprising personally-identifiable data.

18. The method according to claim 1, wherein the non-surgical mode comprises:

a port training mode for establishing the location of a virtual pivot point about which the instrument is restricted to pivot when inserted through the port;

an instrument adjust mode for adjusting the instrument towards a position in which robotic control of the instrument by the operator is enabled; and an instrument change mode for changing an instrument.

19. The data anonymiser system according to claim 12, wherein the non-surgical mode comprises:

a port training mode for establishing the location of a virtual pivot point about which the instrument is restricted to pivot when inserted through the port;

an instrument adjust mode for adjusting the instrument towards a position in which robotic control of the instrument by the operator is enabled; and an instrument change mode for changing an instrument.

* * * * *